United States Patent
Deschamps et al.

(10) Patent No.: US 9,217,728 B2
(45) Date of Patent: Dec. 22, 2015

(54) DEVICE FOR INSPECTING A MOVING METAL STRIP

(75) Inventors: Olivier Deschamps, Mornant (FR); Marc Michaut, L'Horme (FR)

(73) Assignee: SIEMENS VAI METALS TECHNOLOGIES SAS, Saint-Chamond (FR)

( * ) Notice: Subject to any disclaimer, the term of this patent is extended or adjusted under 35 U.S.C. 154(b) by 303 days.

(21) Appl. No.: 13/823,786

(22) PCT Filed: Oct. 12, 2010

(86) PCT No.: PCT/EP2010/065269
§ 371 (c)(1),
(2), (4) Date: Mar. 15, 2013

(87) PCT Pub. No.: WO2012/034602
PCT Pub. Date: Mar. 22, 2012

(65) Prior Publication Data
US 2013/0167644 A1 Jul. 4, 2013

(30) Foreign Application Priority Data
Sep. 15, 2010 (EP) .................................... 10290491

(51) Int. Cl.
*G01N 29/14* (2006.01)
*G01N 29/04* (2006.01)
(Continued)

(52) U.S. Cl.
CPC .............. *G01N 29/14* (2013.01); *G01N 29/043* (2013.01); *G01N 29/2412* (2013.01); *G01N 29/27* (2013.01); *G01N 29/30* (2013.01); *G01N 2291/0234* (2013.01); *G01N 2291/0427* (2013.01); *G01N 2291/2632* (2013.01)

(58) Field of Classification Search
CPC . G01N 29/043; G01N 29/2412; G01N 29/27; G01N 29/14; G01N 2291/0234; G01N 2291/2632; G01N 2291/0427
USPC ..................................................... 73/587, 643
See application file for complete search history.

(56) References Cited

U.S. PATENT DOCUMENTS

| 4,689,996 | A |   | 9/1987 | Hüschelrath |
| 5,142,918 | A | * | 9/1992 | Scaysbrook et al. ............ 73/854 |

(Continued)

FOREIGN PATENT DOCUMENTS

| CN | 101281171 A | 10/2008 |
| CN | 201181290 Y | 1/2009 |

(Continued)

*Primary Examiner* — J M Saint Surin
(74) *Attorney, Agent, or Firm* — Laurence Greenberg; Werner Stemer; Ralph Locher

(57) ABSTRACT

A device for inspecting a moving metal strip includes a first electromagnetic acoustic transducer having an ultrasonic wave emitter. The waves emitted from the emitter are emitted to be incident on a first edge of a surface of the strip, and the emitter is not in contact with the strip. A second electromagnetic acoustic transducer is provided and includes an ultrasonic wave receiver. The waves received emerging from an area of the strip surface toward the receiver, the receiver is not in contact with the strip. A processing unit is coupled to the second electromagnetic acoustic transducer to provide an inspection criterion using a signature of the ultrasonic waves measured. The area is located on the strip such that a wave path between the first edge of the strip and the area is aligned in a linear direction mainly transverse to the direction of movement of the strip.

12 Claims, 1 Drawing Sheet

Figure 1:
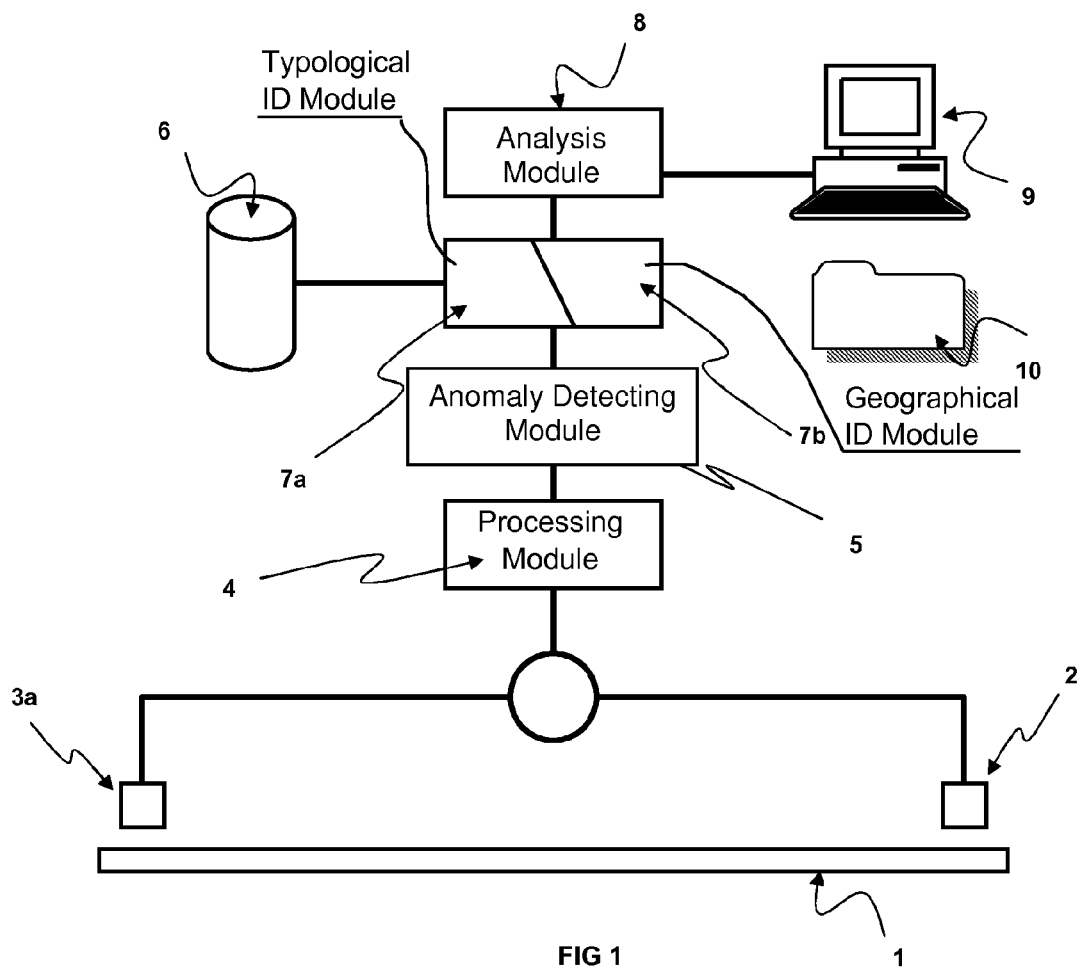

(51) Int. Cl.
*G01N 29/24* (2006.01)
*G01N 29/27* (2006.01)
*G01N 29/30* (2006.01)

(56) References Cited

U.S. PATENT DOCUMENTS

| | | | |
|---|---|---|---|
| 5,154,081 A | | 10/1992 | Thompson et al. |
| 5,439,157 A | * | 8/1995 | Geier et al. ........................ 228/9 |
| 5,714,689 A | | 2/1998 | Latimer et al. |
| 5,866,820 A | | 2/1999 | Camplin et al. |
| 6,122,969 A | * | 9/2000 | MacLauchlan et al. ........ 73/643 |
| 6,138,515 A | | 10/2000 | Moufle et al. |
| 6,234,026 B1 | * | 5/2001 | MacLauchlan et al. ........ 73/643 |
| 6,896,171 B2 | * | 5/2005 | Den Boer et al. ............. 228/103 |
| 6,923,067 B2 | * | 8/2005 | Coen et al. ..................... 73/627 |

FOREIGN PATENT DOCUMENTS

| | | | |
|---|---|---|---|
| EP | 0 885 389 B1 | | 5/2002 |
| EP | 1816468 | * | 8/2007 |
| GB | 1171494 A | | 11/1969 |
| GB | 2139757 | * | 11/1984 |
| JP | S62148851 A | | 7/1987 |
| JP | S62223664 A | | 10/1987 |
| JP | 2002310997 A | | 10/2002 |
| JP | 2004177267 A | | 6/2004 |
| JP | 2006162377 A | | 6/2006 |
| JP | 2007017300 A | | 1/2007 |
| JP | 2008164394 A | | 7/2008 |
| JP | 5215726 A | | 6/2013 |
| WO | 97/33167 A1 | | 9/1997 |

* cited by examiner

DEVICE FOR INSPECTING A MOVING METAL STRIP

BACKGROUND OF THE INVENTION

Field of the Invention

The present invention relates to a device for inspecting a moving metal strip according to the claims.

The invention relates to the contactless inspection of moving metallurgical products, particularly to the detection of internal defects in steel strips, through the use of ultrasonic waves.

The use of ultrasonic waves for the inspection of internal defects in steel structures is known to a person skilled in the art. Numerous variants relating to the type of waves, their frequency and their incidence provide for solutions suitable for very numerous cases of detection of defects presenting in particular locations, orientations and dimensions.

In the majority of cases, inspection relates to fixed structures and is performed by manual or mechanized movement of transducers, i.e. of at least one emitter and at least one receiver of ultrasonic waves on at least one surface of said structure.

The transducers are capable of generating and detecting ultrasonic waves most commonly by implementing the principles of piezoelectricity.

As a general rule, the transfer of ultrasonic waves between the transducer and the structure takes place through an intermediate homogeneous coupling medium, most often aqueous, free from particles and air bubbles, of constant thickness and appropriate viscosity.

The inspection of moving objects such as a moving metal strip or plate poses specific problems essentially associated with the speed of said movement.

One of these problems is the maintenance of effective coupling between the transducer and the surface of the moving object. This is more or less resolved by the transfer of waves between transducer and surface within a column or layer of aqueous couplant such as water or oil or grease or a gel, the column or layer being constantly renewed by a means of couplant circulation or input. Maintenance of the coupling medium is a great constraining obstacle poorly suited to the use of high relative speeds of movement with respect to the transducer and a surface to be inspected.

Another problem relates to the mode of exploration of the object or at least of its surface. In fact, 100% exploration of the surface of a metal strip or plate is very difficult to achieve with ultrasonic waves propagating along a direction substantially perpendicular to said surface. For this purpose, the transducer must move along the width of the strip (transverse to the direction of movement of the strip) and the speed of movement of the strip must be slow enough to allow 100% exploration along a zigzag trajectory resulting from the combined movements of the strip and the transducer, also bearing in mind that the speed of movement of said transducer is limited by the need to maintain a coupling medium. The exercise is therefore highly complex and not suitable for high speeds of strip movement.

Patent EP 0885 389 B1 describes a device used for the detection of defects in a moving metal strip through the use of ultrasonic Lamb waves. In this device, a piezoelectric transducer capable of generating Lamb waves is housed in a wheel preceded by a coupling fluid distribution system. The use of Lamb waves in fact makes it possible to resolve the problem of exploration of the strip, since this specific type of wave is capable of propagating parallel to the surface of the strip. A beam of ultrasonic waves can therefore propagate over the entire width of the strip from a fixed transducer positioned on one of the lateral edges of the moving strip. This type of wave therefore allows far higher speeds of movement of the strip since the exploration is performed over the entire width of the strip and the transducer remains fixed, exploration no longer being performed along a zigzag trajectory. However, the system of exploration by means of contact between the transducer and the strip does not satisfactorily resolve the maintenance of the coupling medium at a high relative transducer/surface to be inspected speed of movement.

Finally, another great problem is that of recognition and evaluation of the defects detected. Involving an inspection of a moving metal strip during its processing, for example by rolling, it is impossible to stop said strip for a period to analyze the defects detected without considerably disrupting the processing.

U.S. Pat. No. 5,866,820 presents a device for inspecting a moving metal strip including:
- a first transducer, also subsequently called EMAT (=electromagnetic acoustic transducer) including an emitter of ultrasonic waves, said waves being emitted so as to be incident from the emitter toward a first surface area of the strip in the vicinity of the transverse strip centre, the emitter not being in contact with the strip,
- a second EMAT including a receiver of ultrasonic waves, said waves being received by emerging from a second area of the strip surface toward the receiver, the receiver not being in contact with the strip, said second area being juxtaposed with the first area along the direction of movement of the strip and allowing for a measurement of the echographic type between the two EMATs,
- a processing unit coupled to the second EMAT so as to provide at least one inspection criterion using an echographic signature of the ultrasonic waves measured at the second EMAT.

This device thus provides for an echographic measurement (by reflection of waves on a defect) over half a strip width. By splitting the device transversely to the direction of movement, it is thus possible to perform an inspection of the entire width of the strip. This latter embodiment thus requires two pairs of two transducers or EMATs, each of the pairs being intended to inspect one half of the strip width.

BRIEF SUMMARY OF THE INVENTION

An object of the present invention is to find a solution to the above mentioned problems, in particular those posed by an inspection of a moving strip using ultrasonic waves, for which the movement of the strip may reach high speeds, such as greater than a m/s. In this respect, the invention aims to avoid any need for constraining contact between a transducer and the strip.

The invention should also provide a simple (for example by limiting the number of transducers for an inspection of the complete strip width) and effective inspection solution for moving metal products, particularly for the detection of internal or surface defects in steel strips, adaptable to the flexible and extensive use of ultrasonic waves such as Lamb, Rayleigh or SH (Shear Horizontal) waves generated and detected without any constraint of contact with the metallurgical product.

Based on a device for inspecting a moving metal strip, including:
- a first transducer (2), also subsequently called EMAT (=electromagnetic acoustic transducer) including an emitter of ultrasonic waves, said waves being emitted so as to be incident from the emitter toward a first edge of a surface of the strip, the emitter not being in contact with the strip, a second EMAT (3a) including a receiver of ultrasonic waves, said waves being received by emerging from an area of the strip surface toward the receiver, the receiver not being in contact with the strip, a processing unit coupled to the second EMAT so as to provide at least one inspection criterion using at least one signature of the ultrasonic waves measured at the second EMAT, the device is characterized in that the area is located on the strip such that a wave path between the first edge of the strip and said area is mainly unidirectional, i.e. aligned in at least one linear direction mainly transverse to the movement of the strip.

In this way, inspection from a desired width up to a complete width of the strip is flexibly possible, and remains in all cases simple since it is performed using only two transducers, neither being in any contact with the strip. The inspection is also advantageously instantaneous (with no zigzag), bearing in mind that the speed of the sound waves between the two transducers is far greater than that of the movement of the strip.

A set of sub-claims also presents advantages of the invention.

In particular, according to a preferred embodiment of the device according to the invention, as far as possible away from the first edge of the strip, the area is located on a strip edge mainly transversally opposite the first edge of the strip. In this way, an inspection of the complete width of the strip is possible, using only two transducers or EMATs. Unlike U.S. Pat. No. 5,866,820, two half-widths aligned on a single strip transversal are thus measurable and it is thus easier to inspect and index a single line (=a transverse width of the strip) of data than two offset portions of lines of inspection data as imposed by U.S. Pat. No. 5,866,820.

Thus, advantageously the first and the second EMATs can present a freely adjustable spacing, equal to or greater than half a strip width.

A preferred embodiment of the inspection device provides for a third EMAT including a receiver of ultrasonic waves transmitted by emerging from a surface of the first edge of the strip toward the receiver, the receiver not being in contact with the strip, the processing unit is thus also coupled to the third EMAT so as to provide at least a second inspection criterion using at least two signatures of the ultrasonic waves, including at least the signature originating from a measurement made by the second EMAT and a signature originating from a measurement made by the third EMAT.

In this way, it is thus possible to obtain a signature by wave echography (between the $1^{st}$ and the $3^{rd}$ EMATs) complementary to the signature by wave transmission (between the $1^{st}$ and the $2^{nd}$ EMATs). The detection of a strip defect by inspection is thus enhanced and the defect can be recognized by two complementary criteria, which aim to eliminate any potential ambiguity with respect to its determination. In fact, one single signature, for example by means of an echographic measurement, may originate from a component of the strip transport device or from the inspection device itself, i.e. be unrelated to an intrinsic strip defect. By providing redundancy of signatures, such components are thus more easily ruled out, making the inspection device more robust against any inspection error.

Ideally, the three EMATs are located at the vertices of a triangle one of the sides of which (between the $1^{st}$ and the 2nd EMAT) is parallel to a transversal to the direction of movement of the strip. The $3^{rd}$ EMAT is placed on the same strip edge as the $1^{st}$ EMAT and slightly offset from the $1^{st}$ EMAT along the direction of movement of the strip. The distance between the $1^{st}$ and the $3^{rd}$ EMAT is defined so as to obtain an ideal triangulation for the desired echographic measurements.

For the purpose of adaptation to a certain strip format and for the purpose of more precise detection of the location of a defect or minimization of areas known as the ultrasonic shadow of inspection according to the invention, at least one of the three EMATs can be designed to be mobile along a direction mainly transverse to the movement of the strip, ideally in slaving mode to a format and/or strip width, making it possible to avoid dangerous interventions in the vicinity of the moving strip.

The device according to the invention also provides that a distance with no contact between each EMAT and the surface of the strip is maintained either constant or, otherwise, is provided by a means of instantaneous measurement, or both in the event, for example, of minor fluctuations in strip thickness or a change from one strip to another.

Finally, the device according to the invention can also provide that at least one wave path between the first edge of the strip and the area is located on a portion of movement of the strip presenting at least one value greater than a minimum strip traction threshold. This quality criterion ensures that fluctuations in the distance with no contact between the strip and the EMATs remain within an acceptable tolerance in order not to confuse a defect with such a fluctuation during an inspection.

The device according to the invention provides that the processing unit includes:
  a module for monitoring the signal-to-noise ratios of the ultrasonic wave measurement signal and/or signals collected at the second and/or third EMAT,
  a module for detecting anomalies in the propagation of ultrasonic waves,
  a means for typological identification of strip areas presenting anomalies in propagation with respect to reference defects stored in a database,
  a means for geographical identification of strip areas presenting anomalies in propagation with respect to a longitudinal origin and a transverse origin of the moving strip,
  a means for identifying the seriousness of defects identified in accordance with at least one criticality threshold taking account of at least one of the geographical and typological identification criteria.

The device according to the invention can include a module to control the generation parameters of waves emitted by the first EMAT capable of being put under a self-calibration mode by executing a series of wave emissions intended to be put under analysis by the processing unit after reception of said series by the second and/or the third EMAT. This self-calibration mode can, however, be replaced or be a calibration mode refined from a calibration databank already predefined by real-time parameterization of a known moving strip.

Finally, another embodiment of the device according to the invention includes:
  at least a fourth EMAT including a wave emitter similar to that of the first EMAT located in the vicinity of the area linked to the second EMAT,
  the first and the fourth EMATs (of the emitter type) can be activated sequentially or even simultaneously under modes free from interference, said modes being measurable sequentially or even simultaneously by the second and the third EMATs (of the receiver type).

In this way, strip defects can be inspected from each edge of the strip, thus the inspection is found to be more exact. In fact, if, from one of the strip edges, i.e. on the basis of one of the EMATs of the emitter type, one signature or signatures of the two associated EMATs of the receiver type will not satisfy a required inspection criterion, two other signatures will be available from the other strip edge, i.e. on the basis of the other EMAT of the emitter type and of the same EMATs of the receiver type. These four signatures (two by wave transmission and two by echography) can be obtained simultaneously (and for the same line or width of the moving strip), since advantageously, the two EMATs of the receiver type can emit streams of ultrasounds, for example at different frequencies, each of which is also simultaneously demodulated without interference by the two EMATs of the receiver type. For this purpose and preferably, the four EMATs can be located at the vertices of a rectangle having a side parallel to a transversal to the direction of movement of the strip.

Finally, the invention also proposes use of the device according to the invention to detect and prevent defects in cold or hot metal strips moving with respect to said device, said defects being either surface or internal and interacting with categories of ultrasonic waves transmitted or reflected as ultrasonic attenuators, diffusers or transformers, the defects being identifiable by at least one signature originating from at least one EMAT including an ultrasonic wave receiver. Such a use of said device is major in providing for the rapid and effective quality control of metal strips produced at a high speed of movement. If such strips are subsequently rolled onto rollers with a view to further metal processing operations, it is thus possible to mark the defective places on the strip which might present a problem or require special processing to ensure the correct conduct of said operations. This is feasible, since the defect signatures can be registered in relation to the strip in question and its typology and topology. At worst, this latter information also makes it possible to locate a precise portion of the strip including at least one defect deemed unfit by the inspection and intended to be cut and removed or reprocessed/recycled.

Exemplary embodiments and applications are provided by means of the following figures:

BRIEF DESCRIPTION OF THE SEVERAL
VIEWS OF THE DRAWING

Figure 2:
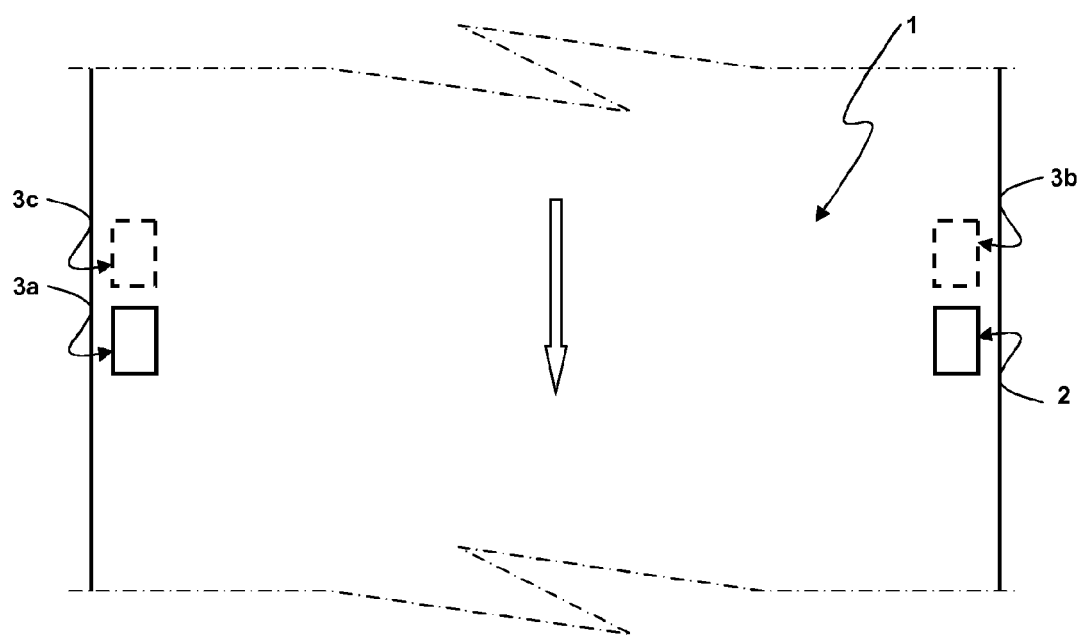

FIG. 1 Schematic front view of the device according to the invention,

FIG. 2 Top view of the arrangement of EMATs according to embodiments of the device according to the invention.

DESCRIPTION OF THE INVENTION

FIG. 1 presents a schematic front view of the device according to the invention. A metallurgical product (1) moves in a metallurgical product processing installation. In our example, the product is a metal strip moving horizontally in a plane perpendicular to FIG. 1.

An ultrasonic wave emitter or generator (2), for example of the EMAT type, positioned here statically above one of the lateral edges of the moving metallurgical product, generates ultrasonic Lamb or Rayleigh or SH (Shear horizontal) waves in said metallurgical product, with no contact with the surface of the latter.

An ultrasonic wave receiver (3a), also of the EMAT type, is positioned statically above the other lateral edge of said product, such that the first and the second EMATs thus defined are opposite one another on a transverse strip line (=strip width).

The receiver (3a) thus receives ultrasonic waves originating from the generator (2) and having passed through a strip width by surface and/or volume transmission of the metal.

A module (4) provides for pre-processing of the signal received from the ultrasonic wave receiver. This processing is intended to enhance the signal-to-noise ratio with a view to more effective use of the signal. It may be, as an example, of the SAFT type (Synthetic Aperture Focusing Technique).

A module (5) provides for the detection of anomalies in the propagation of ultrasonic waves whatever their type, such as attenuation while passing from one edge to the other of the product or return of a reflected echo (see example according to FIG. 2) or transformation of the wave propagation mode.

A database (6) comprises a library of anomalies in the propagation of ultrasonic waves associated with known product defects measured by their similar signatures.

A module (7a) provides for the typological identification of areas presenting propagation anomalies together with the database (6), by implementing, for example, known learning techniques such as k-nearest-neighbor, neural networks, etc.

A module (7b) provides for the geographical identification of areas presenting propagation anomalies with respect to a longitudinal origin and a transverse origin of the moving metallurgical product.

A criticality analysis module (8) provides for the assessment of the seriousness of defects identified in accordance with at least one criticality threshold taking account of at least one of the geographical and typological identification criteria.

These criticality thresholds can be modulated as a function of the level of quality deemed acceptable for a given product, for a given application, a given market, etc. Thus a measured signature may contain quantitative information on the intensity of a defect.

Means (9) of displaying the results of the inspection, for example a monitor linked to data storage made available to an operator, and also output means (10) such as a printer or a plotter, allowing for the immediate or deferred use of the results of the inspection.

FIG. 2 presents a top view of the portion of moving strip on which several possible and advantageous embodiments of the device according to the invention are shown (grouped together).

First of all, the first and the second EMATs including respectively an emitter and a receiver (2, 3a) are represented as in FIG. 1 and form a first embodiment of the device according to the invention.

As an alternative or complement to the receiver (3a), a third EMAT including a second receiver (3b) is positioned statically above the same lateral edge of the metallurgical product as the generator (2). This EMAT arrangement thus forms a second embodiment of the device according to the invention, which makes it possible to obtain two distinct signatures by wave transmission and by echography.

Finally, as an alternative or complement to this second embodiment, a fourth EMAT including a third emitter (3c) is positioned statically above the same lateral edge of the metallurgical product as the first receiver (3a), but offset with respect to it, at least along the direction of movement of the strip. This EMAT arrangement thus forms a third embodiment of the device according to the invention, which makes it possible to obtain two to four distinct signatures by wave transmission between the EMATs on opposite strip edges and additionally by echography between EMATs on the same strip edges. The defect inspection is thus made more refined or more robust with respect to areas of inspection shadow or components external to the inspection device itself.

Depending on the strip formats or the type of defects to be inspected, the static arrangements of the above mentioned EMATs may also be resized in the vicinity of the strip edges according to geometric criteria (variable-angle triangle/trapezium/rectangle), thus providing for a dynamically more efficient inspection in that the ultrasonic signals achieve higher signal-to-noise ratios resulting in more precise defect signatures, which are thus less sensitive to components of adjacent equipment or of the strip.

The ultrasonic wave generator and receivers can thus or also be carried by moving trolleys at least in the direction of the width of the product, thus enabling them to be positioned on the edge or edges of said product whatever its width.

Advantageously, the movement of these moving trolleys is motorized, the motorization being slaved to the width of the metallurgical product and its centering in a processing installation by means of data which are normally known and available in the automatic control system of said installation and said device.

The device according to the invention and the aspects described above thus present a set of decisive advantages with respect to the prior art:
- Absence of contact between the surface of the metallurgical product and the ultrasonic wave generators and receivers, obviating wear on parts rubbing between device and product and also the need to change these rubbing parts regularly,
- No need to distribute coupling product between the surfaces of device and product and thus also no longer any need to clean the surface of products after inspection,
- Operating speed not linked to the need to maintain coupling by contact,
- Simultaneous exploration of all of the width of the metallurgical product,
- Ability to adapt the mode of propagation of the ultrasonic waves to the thickness of the product and to the types of defects being sought,
- Automatic identification and quantification of defects without the need for intervention on the part of an operator, in particular, no need to interrupt the movement of the product to undertake identification,
- Ability to provide information to an operator in real time concerning the quality of the metallurgical product, thus enabling him to eliminate, if necessary, defective areas of the product,
- Ability to output a statement of the quality of the metallurgical product, for example a chart of the defects.

The invention claimed is:

1. A device for inspecting a moving metal strip, the device comprising:
    a first electromagnetic acoustic transducer (EMAT) having an ultrasonic wave emitter, said first EMAT being disposed above a first lateral edge of the metal strip, ultrasonic waves being emitted from said ultrasonic wave emitter being incident on a first edge of a surface of the metal strip, said ultrasonic wave emitter not being in contact with the metal strip;
    a second EMAT having an ultrasonic wave receiver receiving ultrasonic waves originating from said ultrasonic wave emitter of said first EMAT, said second EMAT being disposed at a second lateral edge of the metal strip opposite the first lateral edge, the ultrasonic waves being received emerging from an area of a strip surface disposed toward said ultrasonic wave receiver, said ultrasonic wave receiver not being in contact with the metal strip;
    a processing unit coupled to said second EMAT and providing at least one inspection criterion using at least one signature of the ultrasonic waves measured at said second EMAT; and
    the area of the strip surface disposed on the metal strip such that a wave path between the first edge of the metal strip and the area is aligned in a linear direction mainly transverse to a direction of a movement of the strip.

2. The inspection device according to claim 1, wherein as far as possible away from the first edge, the area is disposed on a strip edge mainly transversally opposite the first edge of the strip.

3. The inspection device according to claim 1, further comprising a third EMAT having a receiver for ultrasonic waves transmitted and emerging from a surface of the first edge of the metal strip toward said receiver, said receiver not being in contact with the metal strip, said processing unit coupled to said third EMAT to provide at least a second inspection criterion using at least two signatures of the ultrasonic waves, including at least a signature originating from a measurement made by said second EMAT and a signature originating from a measurement made by said third EMAT.

4. The device according to claim 3, wherein said first, second and third EMATs are disposed at vertices of a triangle, one side of the triangle being parallel to a transversal to a direction of the movement of the strip.

5. The device according to claim 3, wherein at least one of said first, second and third EMATs is movable along a direction mainly transverse to the movement of the strip.

6. The device according to claim 3, wherein a distance resulting in no contact between each of said first, second and third EMATs and the surface of the metal strip is maintained either constant or, otherwise, and provided by means of instantaneous measurement.

7. The device according to claim 3, wherein said processing unit includes:
    a module for monitoring signal-to-noise ratios of a measurement signal collected at said second EMAT and at said third EMAT;
    a module for detecting anomalies in a propagation of the ultrasonic waves;
    means for typological identification of areas presenting anomalies in propagation with respect to reference defects stored in a database;
    means for geographical identification of areas presenting anomalies in propagation with respect to a longitudinal origin and a transverse origin of the moving metal strip; and
    means for identifying a seriousness of defects identified in accordance with at least one criticality threshold taking account of at least one of geographical and typological identification criteria.

8. The device according to claim 3, further comprising at least one fourth EMAT having a wave emitter identical to that of said first EMAT and disposed in a vicinity of an area linked to said second EMAT, said first and fourth EMATs can be activated simultaneously under modes free from interference, the modes being measurable simultaneously by said second and third EMATs.

9. The device according to claim 8, wherein said first, second, third and fourth EMATs are disposed at vertices of a rectangle having a side parallel to a transversal to a direction of movement of the metal strip.

10. The device according to claim 3, wherein at least one of said first, second and third EMATs is movable along a direction mainly transverse to the movement of the metal strip in a slaving mode to a strip format and/or width.

11. A device for inspecting a moving metal strip, the device comprising:
   a first electromagnetic acoustic transducer (EMAT) having an ultrasonic wave emitter, ultrasonic waves being emitted from said ultrasonic wave emitter being incident on a first edge of a surface of the metal strip, said ultrasonic wave emitter not being in contact with the metal strip;
   a second EMAT having an ultrasonic wave receiver, the ultrasonic waves being received emerging from an area of a strip surface disposed toward said ultrasonic wave receiver, said ultrasonic wave receiver not being in contact with the metal strip, said first and second EMATs being separated by a distance equal to or greater than half a strip width;
   a processing unit coupled to said second EMAT and providing at least one inspection criterion using at least one signature of the ultrasonic waves measured at said second EMAT; and
   the area of the strip surface disposed on the metal strip such that a wave path between the first edge of the metal strip and the area is aligned in a linear direction mainly transverse to a direction of a movement of the strip.

12. A method for detecting and preventing defects, which comprises the steps of:
   providing a device for inspecting a moving metal strip, the device containing:
      a first EMAT having an ultrasonic wave emitter, the first EMAT being disposed above a first lateral edge of the metal strip, the ultrasonic wave emitter not being in contact with the moving metal strip;
      a second EMAT having an ultrasonic wave receiver not being in contact with the moving metal strip, the second EMAT receiving ultrasonic waves originating from the ultrasonic wave emitter of the first EMAT, the second EMAT being disposed at a second lateral edge of the metal strip opposite the first lateral edge; and
      a processing unit coupled to the second EMAT and providing at least one inspection criterion using at least one signature of the ultrasonic waves measured at the second EMAT; and
   moving the metal strip with respect to the device, defects being either surface defects or internal defects interacting with categories of ultrasonic waves transmitted or reflected as ultrasonic attenuators, diffusers or transformers, the defects being identifiable by at least one signature originating from at least one of the EMATs including the ultrasonic wave receiver.

* * * * *